US00PP08262P

United States Patent [19]

Dehan

[11] Patent Number: Plant 8,262

[45] Date of Patent: Jun. 15, 1993

[54] IMPATIENS PLANT NAMED DANDIN

[75] Inventor: Klara Dehan, Holon, Israel

[73] Assignee: Danziger - "Dan" Flower Farm, Moshav Mishmar Hashiva, Israel

[21] Appl. No.: 743,124

[22] Filed: Aug. 9, 1991

[51] Int. Cl.[5] ..... A01H 5/00
[52] U.S. Cl. ..... Plt./87.6
[58] Field of Search ..... Plt./87.6

*Primary Examiner*—James R. Feyrer
*Attorney, Agent, or Firm*—Foley & Lardner

[57] ABSTRACT

A new cultivar of Impatiens plant named Dandin characterized by its large dark pink flowers, relatively small dark green leaves with purple venation, light green stems, unique combination of foliage and flower color, and by its highly floriferous habit.

1 Drawing Sheet

The present invention relates to a new and distinctive cultivar of Impatiens plant, botanically known as Impatiens, and known by the cultivar name Dandin. The new invention was developed by me through controlled breeding by crossing the cultivar designated by breeding number N-19 as the female parent with the cultivar designated 87-209 as the male parent. Both parents are unreleased, proprietary lines.

Asexual reproduction of Dandin by cuttings taken at Mishmar Hashiva, Israel has shown that the unique features of this new Impatiens are stabilized and are reproduced true to type in successive propagations. The cuttings preferably comprise tip cuttings with at least one axillary bud, which is vegetative and not a flower bud.

The following characteristics distinguish the new impatiens from both its parent varieties and other cultivated Impatiens of this type known and used in the floriculture industry:

1. Medium size plant.
2. Relatively small leaves which are dark green tending to red.
3. Large dark pink flowers.
4. The contrast in colors between the foliage and the flowers is unique with respect to other varieties with which applicant is familiar.
5. Floriferous habit.
6. Relatively light green stems.

The accompanying colored photographs illustrate the overall appearance of this cultivar, showing the colors as true as it is reasonably possible to obtain in colored reproductions of this type.

The photograph at the top of the sheet is a top perspective view of a portion of a plant of Dandin, with the floriferous habit being particularly evident.

The petal color in this photograph is lighter than actual color due to light reflection from the petal surfaces.

The bottom photograph is an enlarged showing of a flower, accurately depicting the true flower color.

The following is a detailed description of my new impatiens cultivar based on plants produced under commercial practice during the spring in Mishmar Hashiva, Israel.

Color references are made to The Royal Horticultural Society Colour Chart except where general terms of ordinary dictionary significance are used.

Parentage:

*Male parent.*—87-209.

*Female parent.*—N-19.

Propagation:

A. *Type cutting.*—Leaves without flower buds.

B. *Time to initiate roots.*—8-10 days both at 25°-30° C. summer, and 20°-22° winter.

C. *Rooting habit.*—Good root initiation.

Plant description:

A. *Form.*—Medium size symmetrical plant with very dense flowering.

B. *Habit of growth.*—Compact, good branching, early flowering.

C. *Foliage description.*—(1) Size: Approximately 7.5 cm long and 3.5 cm wide. (2) Shape: Oval, base ovate, tip acuminate. (3) Margin: Finely serrated. (4) Color: Young foliage top side 147A; under side closest to 177A but clearly different. Mature foliage top side 139A; under side 148A. (5) Venation: Purple.

Flowering description:

A. *Flowering habits.*—It takes about 4-5 days from bud to bloom; flowers continuously.

B. *Natural flowering season.*—Natural flowering in the spring and summer in moderate climates. In Israel, it also flowers in winter.

C. *Flower buds.*—Normal. Spurs up to 3.0 cm long on mature buds with throat originating from major sepal; the oval part of the spur is 1.0 cm by 0.6 cm and close to 60C-D in color; the long part is approximately 3.0 cm in length and 0.2 cm wide, curved, and approximately 60C-D.

D. *Flowers borne.*—Flower buds are presented at the tips of stems overlying the terminal whorls of leaves. At most stems, there are generally about 5-6 buds in different stages of maturity, and normally about 1-2 or more open blooms, as the plant reaches market stage.

E. *Quantity of flowers.*—The total number of flowers which are open at the same time is at least 30-35, with flowering as a result being very dense.

F. *Petals.*—(1) Shape: Two pairs, heart shaped; one pair is large and the other smaller; there is one single petal slightly different in shape. (2) Color: Top side in spring when opening 68A, with no fading under side 57C. (3) Number of petals:

Five. (4) Size of flowers: Large approximately 6.0 cm in diameter.

G. *Reproductive organs.*—(1) Stamens: One in number. (a) Anther color: Purple. (b) Pollen color: White. (2) Pistils: (a) Stigma: Cone shaped; green in color. (b) Style: Light Green in color. (c) Ovaries: One in number; size 1.5 mm.

Disease resistance: Good to date.

Other important characteristics: The color of the stems are light green.

I claim:

1. A new and distinct cultivar of Impatiens named Dandin, as illustrated and described.

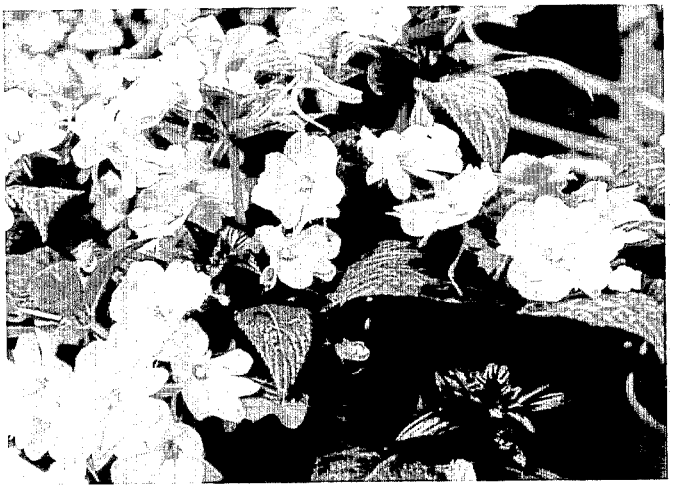
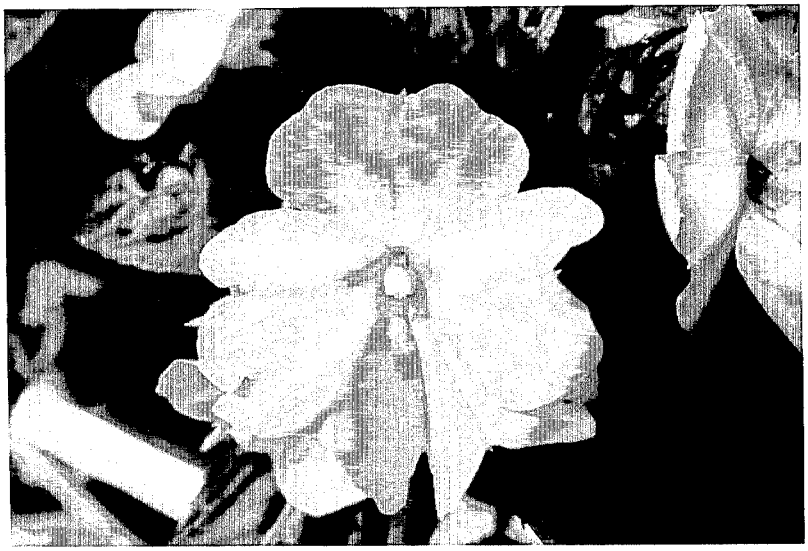

* * * * *